United States Patent [19]

Danielewicz et al.

[11] 4,029,792

[45] June 14, 1977

[54] (2-IMIDAZOLIN-2-YLAMINO) SUBSTITUTED -QUINOXALINES AND -QUINAZOLINES AS ANTIHYPERTENSIVE AGENTS

[75] Inventors: John C. Danielewicz, Ash; Michael Snarey, Sandwich; Geoffrey N. Thomas, Deal, all of England

[73] Assignee: Pfizer Inc., New York, N.Y.

[22] Filed: Sept. 16, 1975

[21] Appl. No.: 613,808

Related U.S. Application Data

[60] Continuation-in-part of Ser. No. 551,318, Feb. 20, 1975, abandoned, which is a division of Ser. No. 332,485, Feb. 14, 1973, Pat. No. 3,890,319.

[30] Foreign Application Priority Data

Nov. 8, 1972 United Kingdom ............ 51629/72
Feb. 29, 1972 United Kingdom ............ 9196/72

[52] U.S. Cl. ................................. 424/251; 424/250
[51] Int. Cl.$^2$ .............. A61K 31/505; A61K 31/495
[58] Field of Search ............................ 424/251, 250

[56] References Cited

UNITED STATES PATENTS

| | | | |
|---|---|---|---|
| 3,560,501 | 2/1971 | Walker | 260/256.4 Q |
| 3,594,380 | 7/1971 | Sulkowski | 260/256.4 Q |
| 3,736,297 | 5/1974 | Bracke | 260/256.4 Q |

Primary Examiner—Albert T. Meyers
Assistant Examiner—Daren M. Stephens
Attorney, Agent, or Firm—Connolly and Hutz

[57] ABSTRACT

Novel (2-imidazolin-2-ylamino) substituted quinoxalines and -quinazolines, their preparation and use as antihypertensive agents are described.

9 Claims, No Drawings

(2-IMIDAZOLIN-2-YLAMINO) SUBSTITUTED -QUINOXALINES AND -QUINAZOLINES AS ANTIHYPERTENSIVE AGENTS

CROSS REFERENCE TO RELATED APPLICATION

This application is a continuation-in-part of Ser. No. 551,318 filed Feb. 20, 1975 and now abandoned, which is in turn a division of application Ser. No. 332,485, filed Feb. 14, 1973, and now U.S. Pat. No. 3,890,319.

BACKGROUND OF THE INVENTION

The invention relates to therapeutic agents which are novel derivatives of quinoxaline or quinazoline, and is particularly concerned with derivatives thereof having a 2-imidazolin-2-ylamino group attached to the homocyclic ring which are useful as regulators of the cardivascular system and, in particular, in the treatment of hypertension.

SUMMARY OF THE INVENTION

The novel compounds according to the invention are those having the general formulae:

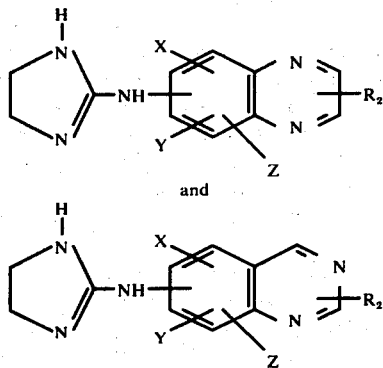

and in which the 2-imidazolin-2-ylamino group may be in any of the 5-, 6-, 7- or 8-positions in the quinoxaline or quinazoline nuclei;

X, Y and Z represent up to 3 optional substituents in any of the remaining 5-, 6-, 7- or 8 positions, each of X,Y and Z being selected from the group consisting of hydrogen, halogen, lower alkyl, lower alkoxy or trifluoromethyl; and $R_2$ represents an optional substitutent in either of the 2- or 3-, or 2- or 4 positions of the quinoxaline or quinazoline nuclei, respectively, $R_2$ being selected from the group consisting of hydrogen, lower alkyl or lower alkoxy; and their pharmaceutically-acceptable acid addition salts.

In this specification "lower" alkyl or alkoxy groups are those containing up to 6 carbon atoms, and "halogen" means fluorine, chlorine, bromine or iodine.

Pharmaceutically-acceptable acid addition salts of the compounds of the invention are those formed from acids which form non-toxic addition salts containing pharmaceutically-acceptable anions, such as the hydrochloride, hydrobromide, hydroiodide, sulphate or bisulphate, phosphate or acid phosphate, acetate, maleate, fumarate, oxalate, lactate, tartrate, citrate, gluconate, saccharate and p-toluene sulphonate salts.

DETAILED DESCRIPTION OF THE INVENTION

The compounds of the invention may be prepared by (1) reaction of the appropriate amino -quinoxaline or -quinazoline (Q—NH$_2$) with thiophosgene to form the corresponding isothiocyanate, (2) reacting the latter with excess ethylene diamine to form the corresponding $\beta$-aminoethyl-thioureido-quinoxaline or -quinazoline, and (3) cyclizing to form the corresponding 2-imidazolin-2-ylamino compound, according to the reaction sequence:

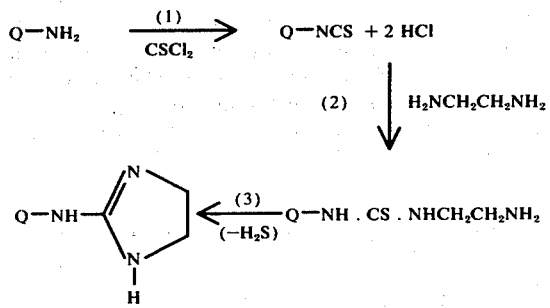

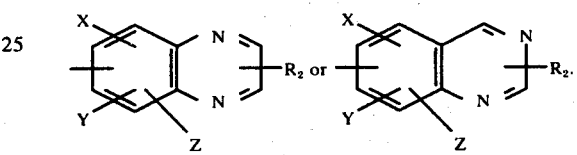

where Q represents a group of the formula:

In step (1) the reaction with thiophosgene can be carried out in aqueous solution or in dilute aqueous hydrochloric acid solution at room temperature in a period of about 2 hours. Alternatively, the thiophosgene can be added to a mixture of an aqueous solution of a weak base, e.g., sodium carbonate, and a solution of the amine Q—NH$_2$ in a water-immiscible solvent, e.g., chloroform. In the first alternative, the isothiocyanate precipitates from the reaction mixture and precipitation can be completed by neutralization with excess alkali; the precipitate is recovered by filtration and, if necessary, basified, and may then be dissolved in a suitable solvent, e.g., chloroform. In the second alternative, the isothiocyanate is formed in solution in the water-immiscible solvent which is then separated. In either case, the solution of the isothiocyanate is dried, filtered, and evaporated to yield the isothiocyanate product as the free base.

In step (2) the isothiocyanate is reacted with an excess (e.g., 5 moles) of ethylene diamine in a suitable solvent, e.g., diethyl ether, benzene, chloroform or dioxan. The reaction is carried out at room temperature in a period of about 2 hours. The $\beta$-aminoethyl-thioureido compound precipitates and is recovered by filtration and washing with further solvent.

In step (3) the cyclization may be effected by heating a suspension of the thioureido compound with mercuric or cupric oxide in a suitable organic solvent medium, e.g., ethanol. The mercuric or cupric oxide can be replaced by an organic mercuric or cupric salt soluble in the medium, e.g., mercuric or cupric acetate. The reaction mixture is filtered, to remove the mercuric or cupric sulphide formed as by-product, and the filtrate is evaporated to dryness. The product may then be recrystallized as the free base or converted to an acid addition salt by reaction with a suitable acid by conventional means.

In certain cases, the cyclization may be successfully effected by simply refluxing the thioureido compound in a suitable organic solvent medium, e.g., methanol, in the absence of mercuric or cupric oxide.

The compounds of the invention can also be prepared by (1) reaction of the corresponding amino -quinoxaline or -quinazoline with benzoyl isothiocyanate to form the corresponding N-benzoyl thioureido compound, followed by hydrolysis to the thioureido compound, or reaction of the amino-quinoxaline or -quinazoline with ammonium thiocyanate to form the thioureido compound directly; (2) methylation to form the S-methyl derivative of the thioureido compound; and (3) reaction with ethylene diamine, according to the reaction sequence:

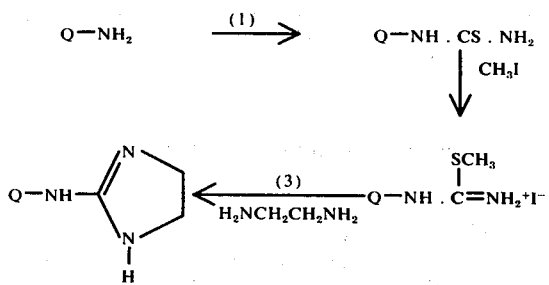

where Q is as previously defined.

For step (1), the benzoyl isothiocyanate starting material can be prepared in situ by reacting benzoyl chloride with ammonium thiocyanate. This may be conveniently carried out by heating under reflux a mixture of the reagents dissolved in a suitable organic solvent, e.g., acetone, for a short period, e.g., 20 minutes. To the cooled solution is then added the appropriate amino -quinoxaline or -quinazoline, and heating under reflux continued for a further period. Precipitation of the product, if it has not already occurred, can then be induced by adding the cooled reaction mixture to water, and the crude product is suitably collected by filtration and used directly in the subsequent hydrolysis step.

Hydrolysis is conveniently achieved by heating the (3-benzoylureido)quinoxaline or -quinazoline in aqueous sodium hydroxide solution for several hours, and the product isolated by filtering the reaction mixture to remove any precipitated sodium benzoate and other solid material and collection of the precipitate formed in the cooled filtrate, if necessary, after further basification. Purification of the resulting thioureido product by recrystallization from a suitable solvent, e.g., butan-2-one, may optionally be effected.

In the alternative method the amino -quinoxaline or -quinazoline is reacted with ammonium thiocyanate to form the thioureido compound directly. This can be achieved by heating a solution of the reagents in water until the product has precipitated. The product, the thioureido compound, is then separated by filtration and optionally purified by crystallization before use in the next step.

In step (2), the thioureido compound is reacted with methyl iodide in a suitable solvent, e.g., methanol. The reaction is conveniently carried out by heating, e.g., in a steam bath, for a short period, e.g., 1 hour, and the product isolated by evaporation of the filtrate from filtration of the reaction mixture.

In step (3), the crude product of the previous stage, conveniently used without the necessity for purification, is dissolved in a suitable solvent, e.g., methanol, and the solution added to a boiling solution of ethylene diamine in the same solvent. The reaction is promoted by heating the solution for several hours, and the resulting precipitate collected by filtration and basified, e.g., using concentrated aqueous ammonium hydroxide solution, to afford the free base form of the required (2-imidazolin-2-ylamino) -quinoxaline or -quinazoline product.

The product may then be recrystallized to purity as the free base or converted to an acid addition salt by reaction with a suitable acid by conventional means.

The amino -quinoxaline or -quinazoline starting materials for these reaction sequences are either readily available materials or are readily preparable from such materials, e.g., by reduction of the corresponding nitro -quinoxaline or -quinazoline and by halogenation of amino -quinoxalines or -quinazolines.

Compounds of the invention in which at least one of X, Y or Z is halogen can also be prepared from the corresponding des-halo compounds by conventional halogenation procedures.

The invention is illustrated by the following examples, in which all temperatures are given in ° C.

EXAMPLE I

To a vigorously stirred solution of 7-amino-8-chloro-4-methoxy quinazoline hydrochloride (3.0 g) in distilled water (150 ml.) was added thiophosgene (1.0 ml.) in one portion. The solution was stirred for 17 hours at room temperature, and the resultant precipitate collected by filtration, washed with water, and dried to afford 1.0 g of 8-chloro-7-isothiocyanate-4-methoxyquinazoline as free base, m.p. 240° with decomposition.

The isothiocyanate prepared as above (1.0 g) was dissolved in a mixture of chloroform (100 ml.) and methanol (200 ml.), and added dropwise to a well stirred solution of ethylene diamine (1.0 g) in chloroform (100 ml.). After stirring at room temperature for 5 hours, the solution was evaporated to dryness. Trituration of the resulting orange oil with water yielded 0.4 g of 1-(2-aminoethyl)-3-(8-chloro-4-methoxyquinazoline-7-yl)thiourea as a white solid, m.p. 230°–232°.

A suspension of the thiourea prepared above (0.4 g) in ethanol (50 ml.) was stirred under reflux conditions (78°) with mercuric oxide (0.5 g) for 4 hours and filtered while hot. Evaporation of the filtrate yielded a white solid which was recrystallised from ethanol to give 0.1 g of 8-chloro-7-(2-imidazolin-2-ylamino)-4-methoxyquinazoline as a free base, m.p. 238°–239°.

Analysis: Found: C, 51,73; H, 4.64; N, 25.06%. Required for $C_{12}H_{12}ClN_5O$: C, 51.90; H, 4.36; N, 25.22%.

EXAMPLE II

A. 6-Amino-5-bromoquinoxaline hydrobromide (10 g.) [prepared by the bromination of 6 -aminaquinoxaline and characterized as the free base (mp 155°–156° C)] was dissolved in water (150 ml.) and thiophosgene (3 ml.) was added. The solution was stirred for 2 hours at room temperature, and the resultant precipitate collected by filtration, washed with water, and dried to afford 9 g. of 5-bromo-6-isothiocyanatoquinoxaline, which was used without further purification in the next stage.

B. The product of (A) (9 g.) was dissolved in benzene (400 ml.) and the solution added to a stirred solution of ethylene diamine (15 g.) in benzene (50 ml.).

During a period of 2 hours with continual stirring an oil separated as a lower layer. The upper benzene layer was poured off and the oil washed with diethyl ether and then dissolved in methanol (approximately 500 ml.). After the methanolic solution had been refluxed until hydrogen sulphide evolution had ceased, it was concentrated by evaporation in vacuo to a volume of approximately 100 ml., by which stage a yellow precipitate had formed. The precipitate was collected by filtration and recrystallized from methanol to afford 3 g. of 5-bromo-6-(2-imidazolin-2-ylamino)quinoxaline, m.p. 250°–251°.

Analysis: Found: C, 45.39; H, 3.35; N, 25.55%. Required for $C_{11}H_{10}BrN_5$: C, 45.22; H, 3.45; N, 23.97%.

EXAMPLES III and IV

By similar procedures to that described in Example II the corresponding 5-chloro- and 5-iodo- compounds, 5-chloro-6-(2-imidazolin-2-ylamino)quinoxaline, m.p. 240°, and 6-(2-imidazolin-2-ylamino)-5-iodoquinoxaline, m.p. 227°, with decomposition, were prepared from 6-amino-5-chloroquinoxaline and 6-amino-5-iodoquinoxaline, respectively, in each case as the hydrochloride salt.

Analyses: Found: C, 52.98; H, 4.09; N, 28.09%. Required for $C_{11}H_{10}ClN_5$ (5-chloro- compound): C, 53.34; H, 4.07; N, 28.28%. Found: C, 38.69; H, 3.08; N, 21.01%. Required for $C_{11}H_{10}IN_5$ (5-iodo- compound): C, 38.95; H, 2.97; N, 20.65%.

EXAMPLE V

The following compounds are prepared from the appropriately substituted aminoquinazoline by the procedure of Example I, the product being isolated in each case as the free base.

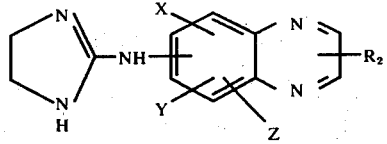

| Al | X | Y | Z | R₂ |
|---|---|---|---|---|
| 5- | H | H | H | H |
| 6- | H | H | H | H |
| 6- | H | H | H | 4-OC₂H₅ |
| 6- | 5-OCH₃ | H | 8-OCH₃ | H |
| 7- | H | H | H | H |
| 8- | H | H | H | H |
| 8- | H | H | H | 4-OCH₃ |
| 7- | H | 6-OCH₃ | H | H |
| 7- | H | 6-OCH₃ | H | 4-OCH₃ |

EXAMPLE VI

Repetition of the procedure of Example I, but using the appropriate aminoquinoxaline hydrochloride in place of 5-amino-8-bromo-6-methylquinoline hydrobromide produces the following compounds:

| Al | X | Y | Z | R₂ |
|---|---|---|---|---|
| 5- | H | H | H | H |
| 5- | H | H | 8-OC₂H₅ | H |
| 5- | 6-OCH₃ | H | H | H |
| 5- | H | H | 8-OCH₃ | H |
| 5- | H | 7-CH₃ | H | H |
| 5- | H | 7-OCH₃ | H | H |
| 5- | 6-OCH₃ | 7-OCH₃ | H | H |
| 6- | H | H | H | H |
| 6- | H | H | H | 2-CH₃ |
| 7- | H | H | H | 2-CH₃ |
| 7- | 5-OCH₃ | H | H | H |
| 7- | H | 6-CH₃ | H | H |
| 5- | H | H | H | 2-CH₃ |
| 8- | H | H | H | 2-CH₃ |

The quinoxalines and quinazolines substituted in the homocyclic portion of the nuclei with both an amino group and one or two halogen atoms, which were used as starting materials in the above preparations, are either known compounds or were themselves prepared from known starting materials according to the following methods, in which all temperatures are given in °C.

EXAMPLE VII

Salt Formation

The free base form of the appropriate (2-imidazolin-2-ylamino) substituted quinoxaline or quinazoline compound in a suitable solvent, e.g., methanol, ethanol, benzene, ether or water, is treated with a stoichiometric amount of the appropriate acid, warming if necessary to achieve reaction. The acid salt is recovered by filtration or evaporation of the solvent.

In this manner, the hydrochloride, hydrobromide, hydroiodide, acetate, maleate, fumarate, oxalate, lactate, tartrate, citrate, gluconate, saccharate, p-toluenesulphonate, sulfate, bisulfate, phosphate and acid phosphate salts of the herein described products are prepared.

In instances such as Examples III and IV wherein the product is obtained as a hydrochloride salt, the free base is obtained by careful neutralization of the acid component with ammonium hydroxide.

METHOD A

To a stirred solution of 7-amino-4-methoxy quinazoline (2.46 g) in glacial acetic acid (90 ml.) at room temperature was added a solution of sulphonyl chloride (2.3 g) in glacial acetic acid (10 ml.) dropwise. The resulting solution was stirred for 1 hour at room temperature after which the precipitated solid was collected by filtration and washed with diethyl ether to afford 3.3 g of 7-amino-8-chloro-4-methoxyquinazoline hydrochloride as a white solid, m.p. 166°–167°. This compound was used directly without further purification in Example 1.

The starting material for Example III, 6-amino-5-chloro-quinoxaline hydrochloride (m.p. 139°–140° C characterised as the free base) was also prepared by this method.

METHOD B

To a stirred solution of 6-aminoquinoxaline (3 g.) in glacial acetic acid at room temperature was added dropwise over a period of one minute a solution of iodine monochloride (4.5 g.) in glacial acetic acid (15 ml.). Stirring at room temperature was continued for a further 30 minutes, after which the precipitated solid was collected by filtration and washed with diethyl ether to afford 6.5 g. of 6-amino-5-iodoquinoxaline hydrochloride, as a complex with iodine, m.p. 167°–169° with decomposition.

Analysis: Found: C, 21.79; H, 1.58; N, 9.66%. Required for $C_8H_6IN_3.I.HCl$: C, 22.11; H, 1.63; N, 9.67%.

This compound was used in Example IV.

The starting materials for Examples II, V and VI are all previously known compounds.

The antihypertensive activity of the compounds of the invention is shown by their ability to lower the blood pressure of conscious hypertensive rats and dogs, when administered subcutaneously and orally, respectively, within the dosage range 0.025–10 mg./kg.

By virtue of their performance in such trials in animals, the preferred compounds of the invention are those in which at least one of X, Y or Z is a halogen atom, and those in which the 2-imidazolin-2-ylamino group is in either the 6- or the 7-position in the quinoxaline or quinazoline nucleus. When any of X, Y or Z is a halogen atom, this is preferably a bromine atom.

Particularly preferred compounds of the invention are those of any of the three formulae given hereinbefore in which the 2-imidazolin-2-ylamino group is in the 6-position and one of X, Y or Z represents a single halogen atom in the 5-position or in which the 2-imidazolin-2-ylamino group is in the 7-position and one of X, Y or Z represents a single halogen atom in the 8-position.

Of particular value as antihypertensive agents have been found to be the compounds of Examples II and III.

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally, for example, intramuscularly or subcutaneously. For parenteral administration, they are best used in the form of a sterile aqueous solution which may contain other solutes, for example, enough salt or glucose to make the solution isotonic.

The compounds of the invention can be administered to humans for the treatment of hypertension by either the oral or the parenteral routes, and may be administered orally at dosage levels within the range 20 µg. to 1.5 mg./day for an average adult patient (70 kg.), given in a single dose or up to 3 divided doses. Intravenous dosage levels would be expected to be about one tenth of the daily oral dose, given in a single quantity. Thus, for an average adult patient, individual oral doses in tablet or capsule form will be in the range from 10 µg to 1.5 mg. of active compound. Variations will necessarily occur depending on the weight and condition of the subject being treated and the particular route of administration chosen.

METHOD C

To a stirred solution of 5-amino-8-methylquinoline (4 g.) in glacial acetic acid (90 ml.) at room temperature was added a solution of sulphuryl chloride (3.5 g.) in glacial acetic acid (10 ml.) dropwise. The solution was stirred for 2 hours at room temperature, and then poured into aqueous sodium acetate solution, resulting in the formation of a precipitate. The latter was collected by filtration and recrystallized from aqueous ethanol solution to afford 2.5 g. of 5-amino-6-chloro-8-methylquinoline as a brown solid, m.p. 113°–114°.

This compound was used directly, without further purification, in Example V.

The following amino- and chloro-substituted quinolines, quinoxalines and quinazolines were prepared by a similar chlorination procedure to that described above. In cases where the hydrochloride salt was isolated, the basification by sodium acetate step was omitted. The example in which the compound was used is indicated in each case.

| Compound | m.p. °C. | Used in Example |
|---|---|---|
| 5-amino-8-chloro-6-methylquinoline | 82° | II |
| 6-amino-5-chloroquinoline hydrochloride | 142–145° | XI |
| 6-amino-5,8-dichloroquinoline hydrochloride (from the 8-chloro-compound | 236–238° | XIV |
| 7-amino-8-chloro-4-methoxyquinazoline hydrochloride | 166–167° | XVII |
| 6-amino-5-chloroquinoxaline | 139–140° | XIX |
| 8-amino-5,7-dichloroquinoline (from 8-aminoquinoline) | 121 | XXI |

What is claimed is:

1. A method for the treatment of hypertension which comprises orally or parenterally administering to a hypertensive host an antihypertensive amount of a compound selected from the group consisting of:

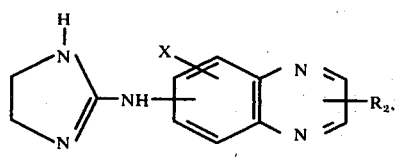

I

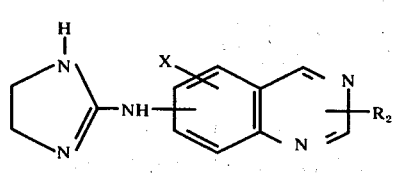

II and the pharmaceutically acceptable acid addition salts thereof wherein X is selected from the group consisting of hydrogen, halogen, lower alkyl, lower alkoxy and trifluoromethyl and $R_2$ is selected from the group consisting of hydrogen, lower alkyl and lower alkoxy.

2. A method according to claim 1 wherein the compound is of formula I.

3. A method according to claim 1 wherein the compound is of formula II.

4. A method according to claim 2 wherein $R_2$ is hydrogen.

5. A method according to claim 2 wherein $R_2$ is hydrogen, X is halogen and the 2-imidazolin-2-ylamino group is located at the 6-position.

6. A method according to claim 5 wherein X is 5-bromo.

7. A method according to claim 5 wherein X is 5-chloro.

8. A method according to claim 3 wherein $R_2$ is hydrogen or 4-methoxy.

9. A method according to claim 3 wherein $R_2$ is hydrogen or 4-methoxy, X is hydrogen and the 2-imidazolin-2-ylamino group is located at the 7-position.

* * * * *